(12) United States Patent
Clement et al.

(10) Patent No.: US 9,693,974 B2
(45) Date of Patent: Jul. 4, 2017

(54) ANTIBACTERIAL AND ANTIFUNGAL BIPHENYLYL COMPOUNDS

(71) Applicant: CHRISTIAN-ALBRECHTS-UNIVERSITY OF KIEL, Kiel (DE)

(72) Inventors: Bernd Clement, Kiel (DE); Franz Furkert, Preetz (DE); Britta Gerig, Munich (DE); Dieter Heber, Molfsee (DE)

(73) Assignee: CHRISTIAN-ALBRECHTS-UNIVERSITY OF KIEL (DE)

( * ) Notice: Subject to any disclaimer, the term of this patent is extended or adjusted under 35 U.S.C. 154(b) by 82 days.

(21) Appl. No.: 14/738,221

(22) Filed: Jun. 12, 2015

(65) Prior Publication Data

US 2015/0272910 A1    Oct. 1, 2015

Related U.S. Application Data

(62) Division of application No. 13/995,261, filed as application No. PCT/EP2011/073601 on Dec. 21, 2011, now abandoned.

(30) Foreign Application Priority Data

Dec. 21, 2010   (DE) .................. 10 2010 055 322

(51) Int. Cl.
| | |
|---|---|
| *A61K 31/14* | (2006.01) |
| *A61K 31/135* | (2006.01) |
| *A61K 33/22* | (2006.01) |
| *C07C 211/29* | (2006.01) |
| *C07C 211/63* | (2006.01) |
| *C07C 225/16* | (2006.01) |

(52) U.S. Cl.
CPC .......... *A61K 31/14* (2013.01); *A61K 31/135* (2013.01); *A61K 33/22* (2013.01); *C07C 211/29* (2013.01); *C07C 211/63* (2013.01); *C07C 225/16* (2013.01)

(58) Field of Classification Search
None
See application file for complete search history.

(56) References Cited

U.S. PATENT DOCUMENTS

| 4,055,664 A | 10/1977 | Skibbe |
| 5,177,067 A | 1/1993 | Guerry et al. |
| 6,710,080 B2 | 3/2004 | Sundermann et al. |

FOREIGN PATENT DOCUMENTS

| DE | 2551591 | 8/1976 | |
| DE | WO 2008003299 A1 * | 1/2008 | ........... A61K 31/135 |
| IT | WO 9959566 A1 * | 11/1999 | ........... A61K 31/198 |
| WO | WO 2008/003299 | 1/2008 | |
| WO | WO 2009/079549 | 6/2009 | |

OTHER PUBLICATIONS

U.S. Appl. No. 13/995,261, filed Jun. 18, 2013, Clement et al.
International Search Report for International (PCT) Patent Application No. PCT/EP2011/073601, mailed Mar. 12, 2012 (with English translation), 5 pages.
Written Opinion for International (PCT) Patent Application No. PCT/EP2011/073601, mailed Mar. 12, 2012 (with English translation), 8 pages.
International Preliminary Report on Patentability for International (PCT) Patent Application No. PCT/EP2011/073601, mailed Mar. 12, 2012 (with English translation), 9 pages.

* cited by examiner

*Primary Examiner* — Yong Chu
(74) *Attorney, Agent, or Firm* — Sheridan Ross P.C.

(57) ABSTRACT

The invention relates to the use of a substance of the general form (I) to produce an antibacterial and/or antifungal drug, wherein X is a methylene group or a carbonyl group; $R_1$, $R_2$, and $R_3$ are each selected from the group comprising hydrogen, an alkyl group having a chain length of 1-4 carbon atoms, an alkoxy group having a chain length of 1-3 carbon atoms, and a halogen; $R_4$ and $R_5$ are each selected from the group comprising hydrogen and an alkyl group having a chain length of 1-4 carbon atoms; and n=3 to 6.

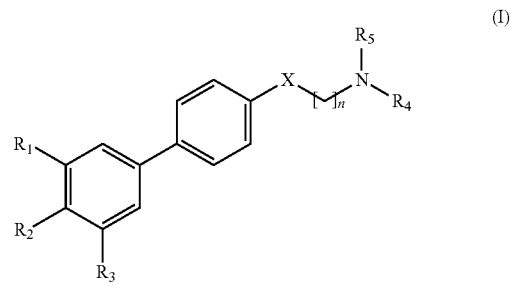

11 Claims, No Drawings

ANTIBACTERIAL AND ANTIFUNGAL BIPHENYLYL COMPOUNDS

CROSS REFERENCE TO RELATED APPLICATIONS

This application is a divisional application of U.S. patent application Ser. No. 13/995,261, filed 30 Aug. 2013, which is a national stage application under 35 U.S.C. 371 and claims the benefit of PCT Application No. PCT/EP2011/073601 having an international filing date of 21 Dec. 2011, which designated the United States, and which PCT application claimed the benefit of German Application No. 102010055322.0 filed 21 Dec. 2010, the disclosure of which is incorporated herein by reference.

The invention relates to antibacterial and antimycotic active substances and their use for production of pharmaceutical compositions.

Despite all scientific progress bacterial infections are a constant threat to mankind.

Today's threat is primarily due to the increase of resistance to conventional antibiotics and the low number of new drugs [Gould, I. M., "Antibiotic resistance: the perfect storm" International Journal of Antimicrobial Agents, 2009, 34 (3), 2-5].

Methicillin-resistant germs represent a specific problem; if a *Staphylococcus aureus* is methicillin-resistant (so-called MRSA) often resistances against antibiotics of other groups (quinolones, tetracyclines, aminoglycosides, erythromycins, sulfonamides) are displayed.

Therefore, the problem underlying the present invention is to provide new compounds which are effective against various bacteria and fungi, especially against those which are already showing multidrug resistance and in this context are suitable as pharmaceutical agents.

It has been shown that basic biphenyls of the general formula

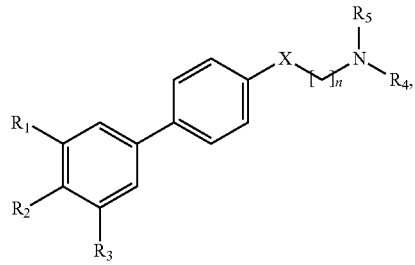

wherein
X is a methylene group ($CH_2$) or a carbonyl group (C=O),
$R_1$, $R_2$ and $R_3$ are hydrogen, an alkyl group having a chain length of 1-4 carbon atoms, (e.g. methyl ($CH_3$)—, ethyl ($CH_2CH_3$)—, propyl ($CH_2CH_2CH_3$)—, isopropyl ($CHCH_3CH_3$)—, butyl ($CH_2CH_2CH_2CH_3$)—, isobutyl ($CHCH_3CH_2CH_3$)— or tert-butyl ($CCH_3CH_3CH_3$)— group), an alkoxy group having a chain length of 1-3 carbon atoms (e.g. a methoxy ($OCH_3$)—, ethoxy ($OCH_2CH_3$)—, propoxy ($OCH_2CH_2CH_3$)— or isopropoxy ($OCHCH_3CH_3$)— group) or a halogen (e.g. Fluorine (F), chlorine (Cl), bromine (Br) or iodine (I)),
$R_4$ and $R_5$ are hydrogen or an alkyl group having a chain length of 1-4 carbon atoms (e.g. methyl ($CH_3$)—, ethyl ($CH_2CH_3$)—, propyl ($CH_2CH_2CH_3$)—, isopropyl ($CHCH_3CH_3$)—, butyl ($CH_2CH_2CH_2CH_3$)—, isobutyl ($CHCH_3CH_2CH_3$)—, or tert-Butyl ($CCH_3CH_3CH_3$)— group) and
wherein n can be n=3-6, as well as salts, hydrochlorides and tautomers of those compounds, have an antimicrobial and antifungal activity also against methicillin-resistant germs. Therefore, the bisphenyls as described above and illustrated in the following embodiments are suitable for inhibiting the growth of bacteria and/or fungi. Accordingly, the present invention relates to the use of the substances as antibacterial and/or antifungal drugs.

Table 1 shows the values of the minimum inhibitory concentration (MIC) of the substances of the present invention. For comparison, the substance GG20-3, which differs from the substances of the present invention by a shortened methylene group chain (n=2) and the known antibiotics vancomycin and tetracycline, were also measured.

Determination of the Minimum Inhibitory Concentration (MIC)

The minimum inhibitory concentration is the lowest concentration of the tested substance which completely inhibits the growth of each test organism, i.e. wherein after incubation the turbidity is not measurable. The respective determination is valid if in the growth control (DMSO and medium) a distinct turbidity is observed.

ABBREVIATIONS

*Staphylococcus aureus* S. a., methicillin-resistant *Staphylococcus aureus* MRSA, *Escherichia coli* E. c., *Pseudomonas aeroginosa* P. a., *Staphylococcus epidermis* S. e., *Candida albicans* C. a., *Enterococcus hirae* E. h., *Aspergillus niger* A. n., *Aspergillus fumigatus* A. f., n. d. not defined.

TABLE 1

| (part 1): MIC values (μg/ml)* | | | | | | |
|---|---|---|---|---|---|---|
| Substance | Code | S.a. | MRSA | E.c. | P.a. | S.e. |
|  | GG20-3 | 32 | 32 | >64 | >64 | 16 |

TABLE 1-continued
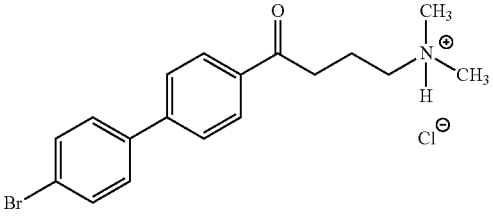 [SMILES: C[NH+](C)CCCC(=O)c1ccc(-c2ccc(Br)cc2)cc1 ; [Cl-]]
| | Code | | | | |
|---|---|---|---|---|---|
| (structure GG20-4) | GG20-4 | 4-8 | 8 | >64 | >64 | 4 |
| (structure GG20-5) | GG20-5 | 16 | 16 | n.d. | n.d. | n.d. |
| (structure GG28) | GG28 | 13 (3) | 18 (3) | n.d. | n.d. | n.d. |
| Vancomycin | | | <2 (2) | | |
| Tetracyclin | | | 64 | | |
(part 2): MIC values (μg/ml)*
| Substance | Code | C.a. (Yeast) | E.h. | A.n. | A.f. |
|---|---|---|---|---|---|
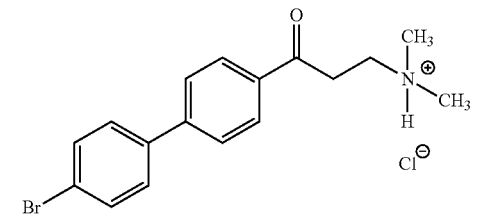 [SMILES: C[NH+](C)CCC(=O)c1ccc(-c2ccc(Br)cc2)cc1 ; [Cl-]]
| | Code | C.a. (Yeast) | E.h. | A.n. | A.f. |
|---|---|---|---|---|---|
| (structure GG20-3) | GG20-3 | 64<br>10 (3) | n.d. | n.d. | n.d. |
| (structure GG20-4) | GG20-4 | 4<br>11 (5) | 16 | 64 | 8 |
| (structure GG20-5) | GG20-5 | 8 | n.d. | n.d. | n.d. |

TABLE 1-continued

| Structure | Compound | Value | | | |
|---|---|---|---|---|---|
| (4-bromophenyl-C6H4-(CH2)4-N+(CH3)2H Cl−) | GG28 | 8 (2) | n.d. | n.d. | n.d. |

*for identification of multiple testings: Representation of rounded average values of logarithmic endpoints, number of tests in brackets.

An unexpected significant increase in the efficacy can be shown in all cases in the transition of the compound GG20-3 with n=2 to compounds in which the chain has been extended by one or more methylene groups (n≥3).

In addition, the high efficacy of the substances of the present invention against various germs, in particular MRSA is observed.

A particular advantage of the compounds of the present invention is their high solubility in water. This is a major benefit in the use of the substances as a drug because on the one hand, the oral bioavailability of the drug is increased, on the other hand the administration by injection of aqueous solutions is possible. In a test trial 100 mg of the compound GG20-4 (see Table 1) could be dissolved in 10 ml of distilled water, wherein the person skilled in art knows that pharmaceuticals are typically administered in combination with pharmaceutically acceptable excipients.

A characteristic example for a substance in accordance with the present invention, which is both antibacterial and antifungal active, is 4'-(4-bromophenyl)-4-dimethylaminobutyrophenone-hydrochloride 1 (GG20-4) with n=3:

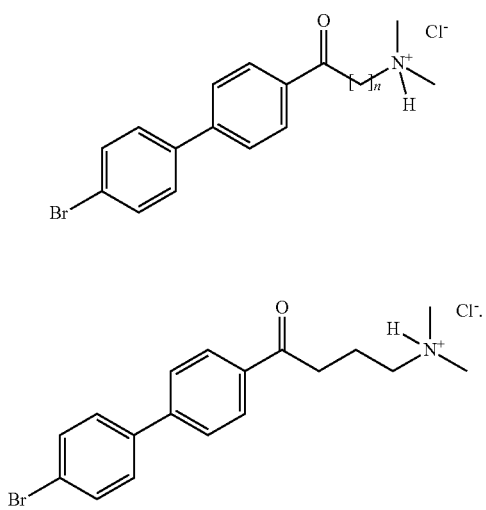

Another example for substances according to the present invention is the compound 4-bromo-4'-(4-dimethylaminobutyl) biphenyl hydrochloride 2 (GG28). This substance is not known in the literature and also has both antibacterial and antifungal activity.

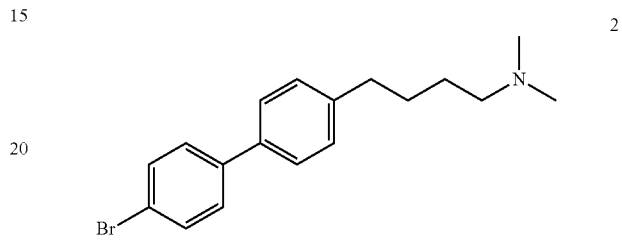

The synthesis of the antimicrobial and antifungal active substances of the present invention are shown in Scheme 1 and 2. They can be produced by conventional methods. The comparative compounds with a chain length of n=2 can be obtained from a reaction of partially substituted acetophenones with dimethylammonium chloride and paraformaldehyde in the sense of a Mannich reaction. Compounds with the chain length of n=3 were obtained by a reaction of substituted 4-chloro-butyrophenone derivatives with dimethylamine in the sense of a nucleophilic substitution. This reaction is exemplified below for the compound 4'-(4-bromophenyl)-4-dimethylaminobutyrophenone hydrochloride 1 (GG20-4):

Scheme 1: Presentation of 4'-(4-bromophenyl)-4-dimethylaminobutyrophenone-hydrochloride 1 (GG20-4).

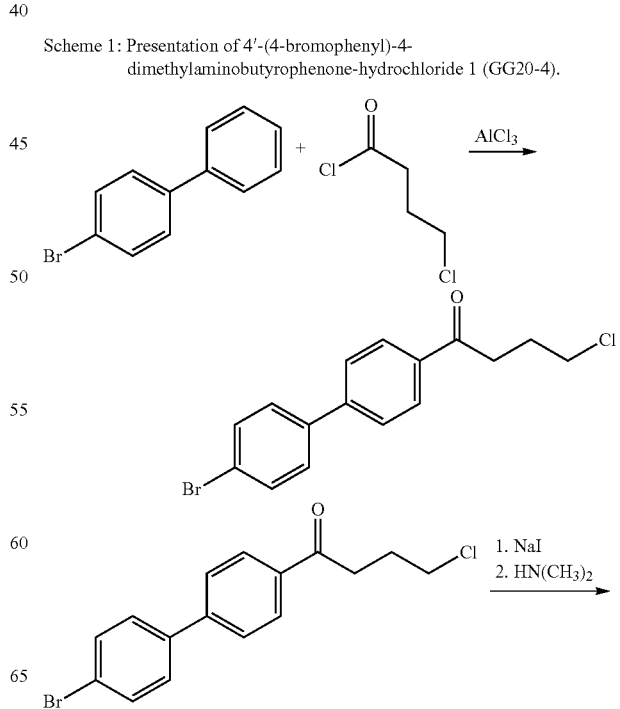

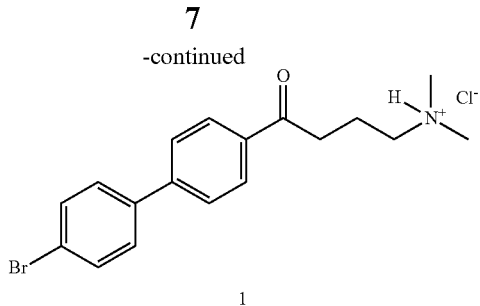

Compounds with a chain length of n=4 were obtained analogously to the reaction with substituted 5-chloro-valerianophenone derivatives with dimethylamine in the sense of a nucleophilic substitution.

The compound 2 was obtained based on the compound 1 in the sense of the Huang-Minlon-Variant of a Wolff-Kishner-Reduction:

Scheme 2: Synthesis of 4-bromo-4'-(4-dimethylaminobutyl) biphenyl hydrochloride 2 (GG28).

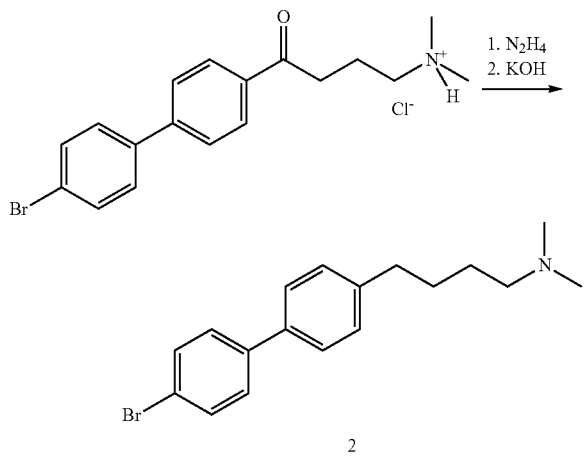

The basic biphenyls of the present invention represent high effective inhibitors of the growth of bacteria and fungi. They can be easily and economically synthesized by standard methods with high purity. Accordingly, the present invention provides compounds for inhibiting the growth of bacteria and/or fungi and, consequently, drugs for the treatment of infections of bacteria and/or fungi.

Studies of analogue compounds with a linker consisting of three, four and five carbon atoms also without ketofunction show that the antibacterial effect is dependent on the length of the side chain. Alternatively, the replacement of the N-dimethylamino group to a N-phenylpiperazino-group leads to loss of activity. In a test experiment a MIC value for 4'-(4-bromophenyl)-4-(N-phenylpiperazino)butyrophenone-hydrochloride could not be determined, since the substance did not inhibit the growth of *Staphylococcus aureus* also after addition of higher concentrations.

Pathogens in the growth phase are killed with lower concentrations as those which are in the dormant phase. In a test experiment, the test germs were once used in the exponential phase of their growth (18 h before incubation), compared to an inoculum which was harvested, and used after 48 h (quiescent period). Cells which were not as capable of dividing, showed a 2-3 fold higher MIC as the active cells. Thus, there are indications that quiescent phase cells are less sensitive.

As evident from the explanations and examples above, the substances of the present invention can also be used as laboratory reagents for inhibiting the growth of bacteria and/or fungi in cell culture, similar as described for the selection marker system neomycin and neomycin-phosphotransferase system.

The preparation in accordance with the present invention is illustrated by way of examples.

Example 1

4'-(4-bromophenyl)-4-dimethylaminobutyrophenone-hydrochloride 1

25.7 mmol (6 g) 4-bromobiphenyl, 25.7 mmol (3.6 g) 4-chloro butyryl chloride and 32.2 mmol (4.2 g) aluminium trichloride are weighed out in a 250 mL piston before 50 mL dryed dichloromethane are added. After stirring overnight at room temperature, the mixture is placed on ice and the precipitated aluminum hydroxide is brought into solution with concentrated hydrochloric acid. Subsequently, the organic phase is separated and extracted with water as long as the water phase shows a neutral pH value. The organic phase is then dried over $Na_2SO_4$, filtered, and the solvent is removed under vacuum. The residuum is recrystallized from a mixture of cyclohexane/ethyl acetate.

1.2 mmol (500 mg) NaI are added to 1.2 mmol (184 mg) of the resulting pure product in 5 mL ethylmethyl ketone and heated for 1½ h at 90° C. in an oil bath. Subsequently, the solution is removed in a vacuum, 1 mL of dimethylamine as well as 30 mL absolute ethanol are added and heated for further 8 h at reflux.

After removing the solvent in the vacuum, ice is added to the residue and the precipitated raw product is aspirated. Recrystallization from cyclohexane/ethyl acetate results 1 in a yield of 82% (377 mg); mp=224° C.

$^1$H-NMR Data (300 MHz, DMSO-$d_6$); 1.94 (m., 2H, —$CH_2$—), 2.8 (s, 6H, N($CH_3$)$_2$), 3.15 (m, 4H, COC$H_2$—; —$CH_2$NH($CH_3$)$_2$), 7.70 (m, 4H, Ar—H); 7.85 (d, $^3J$=8.7 Hz, 2H, H-3', H-5'), 8.04 (d, $^3J$=8.7 Hz; 2H, H-2', H-6'), 9.21 (bs, 1H, NH). $^{13}$C-NMR-Data (75 MHz, DMSO-$d_6$): 18.4 (C-3), 35.0 (C-2), 42.0 (2×$CH_3$), 56.1 (C-4), 122.0 (C-4"), 126.8 (2C, C-3', C-5'), 128.6 (2C, C-2', C-6'), 129.0 (2C, C-2"; C-6"), 131.9 (2C, C-3", C-5"), 135.5 (C-1"), 138.0 (C-1'), 143.2 (C-4'), 198.2 (CO).

Example 2

4-bromo-4'-(4-dimethylaminobutyl)-biphenyl hydrochloride 2

0.02 mol (6.96 g), 1, 5 mL hydrazine monohydrate and 60 mL absolute ethanol are added in a 100 mL piston. Subsequently, it is heated at the reflux until a complete solution occurs (12 h). Afterwards, 40 mL ethanol are removed under vacuum and 40 mL triglycol as well as 10 g of potassium hydroxide and 3 ml hydrazine monohydrate are added. The mixture is heated a further hour at 80° C. (development of gas!) before the temperature is up-regulated until the thermometer indicates 200 to 220° C. The mixture is cooled down and the resulting precipitation is aspirated and recrystallized from ethanol. Yield 85% (5.6 g); mp=245° C.

$^1$H-NMR-Data (300 MHz, CDCl$_3$): 1.39 (m, 2H, —$CH_2$—), 1.62 (m, 2H, —$CH_2$—), 2.27 (s, 6H, N($CH_3$)$_2$), 2.36 (t, $^3J$=8.4 Hz, 2H, —$CH_2$NH($CH_3$)$_2$), 2.55 (t, $^3J$=8.4 Hz, 2H, Ar—$CH_2$—), 7.18 (d, $^3J$=8.7 Hz; 2H, H-2', H-6'); 7.42 (m, 4H, H-3', H-5', H-2", H-6"), 7.48 (d, $^3J$=8.7 Hz; 2H, H-3", H-5"). $^{13}$C-NMR-Data (75 MHz, CDCl$_3$): 27.4 (C-3), 29.0 (C-2), 35.7 (C-1), 45.9 (2×CH$_3$), 59.1 (C-4), 122.0 (C-4"), 127.7 (2C, C-3', C-5'), 128.7 (2C, C-2', C-6'), 130.1 (2C, C-2"; C-6"), 132.2 (2C, C-3", C-5"), 133.7 (C-4'), 135.5 (C-1"), 137.6 (C-1').

The melting points of the synthesized substances were measured with the melting point apparatus Bilchi 510 device and micro hotplate Thermovar (Company Reichert). The NMR spectra were measured with the nuclear magnetic resonance spectrometer Bruker ARX 300 and the IR spectra (as KBr-Pellets) with a Perkin-Elmer FT-IR 16 PC spectrometer. The mass spectra were measured with a device of type Hewlett-Packard 5989. Elementary analysis was performed in the Institute of Inorganic Chemistry, of the CAU Kiel using a CHNS-analyzator of the company Hekatech GmbH. Unless otherwise stated, the chemicals including vancomycin-HCl and tetracycline-HCl at the highest purity were purchased at the company Sigma-Aldrich GmbH.

The minimum inhibitory concentrations of the substances of the present inventions against various infectious germs, i.a. against methicillin-resistant *Staphylococcus aureus* were determined with the Bouillon-microdilution method in accordance with the procedure M07-A8 of the Clinical and Laboratory Standards Institute (Pennsylvania, USA).

Test Organisms (Source: German Collection of Microorganisms and Cell Cultures, Braunschweig) *Enterococcus hirae* ATCC 10541, *Staphylococcus epidermidis* ATCC 12228, *Staphylococcus aureus* ATCC 6538, methicillin-resistant *Staphylococcus aureus* ATCC 33592, *Bacillus cereus* ATCC 11778, *Candida albicans* ATCC 10231, *Aspergillus niger* ATCC 16404, *Aspergillus fumigatus* ATCC 9197.

Test Vessels

Sterile 96-well micro titer plates of plastic with rounded bottoms of the test wells (wells; BRANDPLATES™, Ref. 781960).

Cultivation of Test Organisms

In sterile tubes with titled agar, bacteria with casein peptone soy flour peptone agar (Merck, Art. No. 1.05458.05), incubation 18-24 h at 34° C., fungi with Sabouraud 4% Glucose Agar (Merck 1.05438.05), incubation *Candida albicans* 18-24 h at 34° C., mold fungous 7 days at 22° C.

The long-term cultures of the test organisms are incubated at titled agar at 22° C. and each inoculated after 4 weeks on fresh medium. After every fifth culture passage or ascertainment of impurities the corresponding culture is discarded and newly grown from the lyophilisate.

Production of Inocula

Suspensions are produced on titled agar by floating with 0.9% sterile NaCl solution. The turbidity is adjusted photometrically by dilution according to the turbidity of the Mc Farland-standard 0.5.

Subsequently, the bacterial suspensions are diluted in the ratio of 1:10, the Pi-suspension of the fungi remains undiluted.

The number of the germs in the inocula is adjusted so that there are approximately 5×10$^5$ colony forming units per milliliter after inoculation of the test wells.

Preparing Stock Solutions of the Antibiotics

The amount of a substance to be tested in a trial is weighed out on a microbalance with an Eppendorf reaction vessel and dissolved in an appropriate volume of dimethyl sulfoxide so that the concentration of the resulting solution corresponds to the 21 times highest final test concentration. The stock solution is subsequently diluted in a serial in a ratio respectively 1 ad 2 with DMSO resulting in seven different concentrations in the wells of a predilution plate. In the eighth well only DMSO is pipetted.

Loading the Plates

In each of the 96 wells of a test plate 95 µl sterile Mueller Hinton II medium (Cation adjusted, BBL™ Ref. 212322) for bacteria and sterile Sabouraud 2% glucose medium (DIFCO™ Ref 238230) for fungis are added with an eight-channel pipette (Socorex 50-200 µL). 5 µL of the solution to be tested are pipetted in each of the test wells of the plate (8-channel pipette, Eppendorf-Research, 5-10 µL). They are transferred in this way from the pre-dilutions that in the horizontal row A the highest concentration and respectively a half reduced concentration of the substance to be tested until row G and in row H only DMSO is pipetted. Subsequently, 5 µL of the inocula are pipetted in the test wells using an eight-channel pipette. In one test at least two, maximum four rows are inoculated with the same substance and the same germs. The concentrations of the test substance are each 128 µg/mL to 2 µg/mL.

Evaluation and Incubation of the Microtiter Plates

The prepared plates are converted to a microtiter plate reader (Anthos ht111) which is connected to a printer. In this device, the plates are shaken for 60 seconds with high frequency before each measurement and the absorption of the probes is measured at the wavelength of light of 590 nm.

After determination of the initial values the plates are incubated at 34° C. for 16 to 20 h for bacteria and *Candida albicans*, and 68 to 72 h at 34° C. for mould fungis.

Following this the micro titer plates are measured again as described above.

Determination of the Minimum Inhibitory Concentration (MIC)

The minimum inhibitory concentration is the lowest concentration of the tested substance which is able to inhibit the complete growth of the particular test organism, i.e. where after incubation no turbidity is measurable. The particular determination is valid when in the growth control (DMSO and medium) a distinct turbidity is observed.

The invention claimed is:

1. A method of treating a bacterial and/or fungal infection in an individual comprising administering an effective amount of a substance of the formula

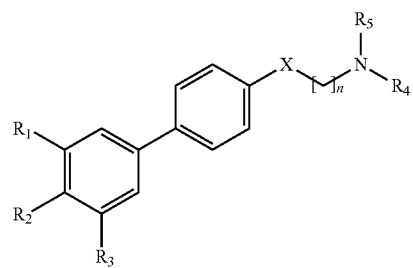

wherein
X is a methylene group;
R$_1$, R$_2$ and R$_3$ are each selected from the group consisting of hydrogen, an alkyl group having a chain length of 1-4 carbon atoms, an alkoxy group with a chain length of 1-3 carbon atoms, and a halogen;
R$_4$ and R$_5$ are each selected from the group consisting of hydrogen and an alkyl group with a chain length of 1-4 carbon atoms; and
n=3 to 6
or a salt thereof to an individual in need thereof.

2. The method of claim 1, wherein the alkyl group in $R_1$, $R_2$, $R_3$, $R_4$ or $R_5$ is a methyl ($CH_3$)—, an ethyl ($CH_2CH_3$)—, a propyl ($CH_2CH_2CH_3$)—, an isopropyl ($CHCH_3CH_3$)—, a butyl ($CH_2CH_2CH_2CH_3$)—, an isobutyl ($CHCH_3CH_2CH_3$)— or a tertiary butyl ($CCH_3CH_3CH_3$)— group.

3. The method of claim 1, wherein the alkoxy group is a methoxy ($OCH_3$)—, an ethoxy ($OCH_2CH_3$)—, a propoxy ($OCH_2CH_2CH_3$)— or an isopropoxy ($OCHCH_3CH_3$)— group.

4. The method of claim 1, wherein the halogen is fluorine (F), chlorine (Cl), bromine (Br), or iodine (I).

5. The method of claim 1, wherein the water-solubility of the substance at room temperature is equal to or greater than 1,000 mg/l.

6. The method of claim 1, wherein the water-solubility of the substance at room temperature is equal to or greater than 5,000 mg/l.

7. The method of claim 1, wherein the water-solubility of the substance at room temperature is equal to or greater than 10,000 mg/l.

8. The method of claim 1, wherein the substance is 4-bromo-4'-(4-dimethylaminobutyl)biphenylhydrochloride having a chemical structural formula:

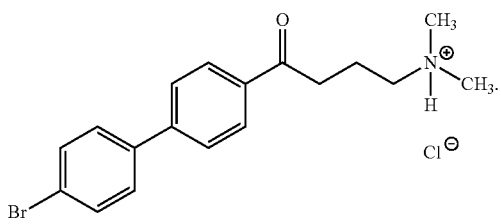 [SMILES: C[NH+](C)CCCC(=O)c1ccc(-c2ccc(Br)cc2)cc1 ; [Cl-]]

9. The method of claim 1, wherein the substance administered is the hydrochloride salt of the formula.

10. A method of treating a bacterial and/or fungal infection in an individual comprising administering an effective amount of a substance of the formula

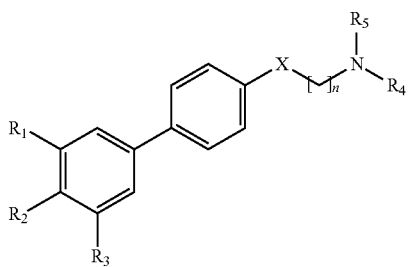

wherein

X is a methylene or a carbonyl group;

$R_1$, $R_2$ and $R_3$ are each selected from the group consisting of hydrogen; an alkyl group selected from a methyl ($CH_3$)—, an ethyl ($CH_2CH_3$)—, a propyl ($CH_2CH_2CH_3$)—, an isopropyl ($CHCH_3CH_3$)—, a butyl ($CH_2CH_2CH_2CH_3$)—, an isobutyl ($CHCH_3CH_2CH_3$)— or a tertiary butyl ($CCH_3CH_3CH_3$)— group; an alkoxy group with a chain length of 1-3 carbon atoms; and a halogen;

$R_4$ and $R_5$ are each selected from the group consisting of hydrogen; and an alkyl group selected from a methyl ($CH_3$)—, an ethyl ($CH_2CH_3$)—, a propyl ($CH_2CH_2CH_3$)—, an isopropyl ($CHCH_3CH_3$)—, a butyl ($CH_2CH_2CH_2CH_3$)—, an isobutyl ($CHCH_3CH_2CH_3$)— or a tertiary butyl ($CCH_3CH_3CH_3$)— group; and n=3 to 6 or a salt thereof to an individual in need thereof.

11. A method of treating a bacterial and/or fungal infection in an individual comprising administering an effective amount of a substance of the formula

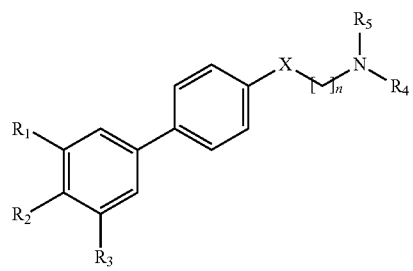

wherein

X is a methylene or a carbonyl group;

$R_1$, $R_2$ and $R_3$ are each selected from the group consisting of hydrogen; an alkyl group having a chain length of 1-4 carbon atoms; an alkoxy group selected from a methoxy ($OCH_3$)—, an ethoxy ($OCH_2CH_3$)—, a propoxy ($OCH_2CH_2CH_3$)— or an isopropoxy ($OCHCH_3CH_3$)— group; and a halogen;

$R_4$ and $R_5$ are each selected from the group consisting of hydrogen, and an alkyl group with a chain length of 1-4 carbon atoms; and n=3 to 6 or a salt thereof to an individual in need thereof.

* * * * *

UNITED STATES PATENT AND TRADEMARK OFFICE
CERTIFICATE OF CORRECTION

PATENT NO. : 9,693,974 B2
APPLICATION NO. : 14/738221
DATED : July 4, 2017
INVENTOR(S) : Bernd Clement et al.

It is certified that error appears in the above-identified patent and that said Letters Patent is hereby corrected as shown below:

In the Claims

In Claim 8, Column 11, please delete the chemical structure in Lines 25-34:

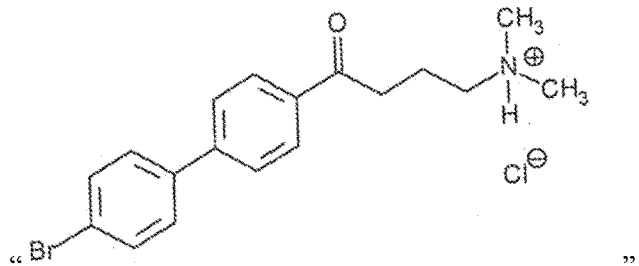

And insert:

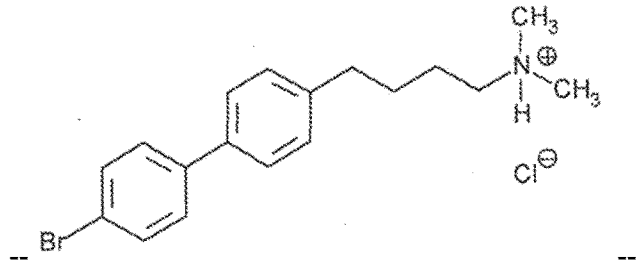

Signed and Sealed this
Eighth Day of January, 2019

Andrei Iancu
*Director of the United States Patent and Trademark Office*